United States Patent
Li et al.

(10) Patent No.: US 10,524,504 B2
(45) Date of Patent: Jan. 7, 2020

(54) ATOMIZER AND ELECTRONIC CIGARETTE HAVING SAME

(71) Applicant: Shenzhen First Union Technology Co., Ltd., Shenzhen, Guangdong (CN)

(72) Inventors: Yonghai Li, Shenzhen (CN); Zhongli Xu, Shenzhen (CN); Shuyun Hu, Shenzhen (CN)

(73) Assignee: SHENZHEN FIRST UNION TECHNOLOGY CO., LTD., Shenzhen, Guangdong Province (CN)

( * ) Notice: Subject to any disclaimer, the term of this patent is extended or adjusted under 35 U.S.C. 154(b) by 483 days.

(21) Appl. No.: 14/797,089

(22) Filed: Jul. 11, 2015

(65) Prior Publication Data
US 2016/0007655 A1    Jan. 14, 2016

(30) Foreign Application Priority Data

Jul. 11, 2014   (CN) ..................... 2014 2 0381903 U

(51) Int. Cl.
| | | |
|---|---|---|
| A24F 47/00 | (2006.01) | |
| A61M 15/06 | (2006.01) | |
| F22B 1/28 | (2006.01) | |
| H05B 3/06 | (2006.01) | |
| H05B 3/22 | (2006.01) | |

(52) U.S. Cl.
CPC ........... *A24F 47/008* (2013.01); *A61M 15/06* (2013.01); *F22B 1/284* (2013.01); *H05B 3/06* (2013.01); *H05B 3/22* (2013.01)

(58) Field of Classification Search
CPC .. A24F 47/008; A61M 11/042; A61M 11/044; A61M 15/06

USPC ................ 131/329; 392/386, 390, 394–398, 392/403–406
See application file for complete search history.

(56) References Cited

U.S. PATENT DOCUMENTS

| 5,505,214 A * | 4/1996 | Collins ................. A24F 47/008 131/194 |
|---|---|---|
| 2012/0199663 A1* | 8/2012 | Qiu ...................... A61M 11/041 239/8 |
| 2013/0152922 A1* | 6/2013 | Benassayag .......... A61M 15/06 128/202.21 |

(Continued)

FOREIGN PATENT DOCUMENTS

| CN | 102861694 | * | 1/2013 | ............. A24F 47/00 |
|---|---|---|---|---|
| WO | WO 2014/079024 | * | 5/2014 | ............. A24F 47/00 |
| WO | WO2014/106329 A1 | * | 7/2014 | ........... A24F 47/008 |

*Primary Examiner* — Tu B Hoang
*Assistant Examiner* — Erin E McGrath
(74) *Attorney, Agent, or Firm* — Cheng-Ju Chiang

(57) ABSTRACT

An exemplary atomizer includes a shell, a liquid supply received in the shell, and an atomizing assembly. The liquid supply is configured for storing tobacco liquid, and the liquid supply has an open end. The atomizing assembly includes a liquid conducting element, a heating disk, and a liquid absorbing body. An end of the liquid conducting element is engaged in the open end. The heating disk is arranged at an opposite end of the liquid conducting element. The liquid absorbing body is sandwiched between the liquid conducting element and the heating disk. The liquid conducting element is configured for conveying the tobacco liquid from the liquid supply to the liquid absorbing body. The heating disk is configured for heating the tobacco liquid in the liquid absorbing body to vaporize.

17 Claims, 3 Drawing Sheets

(56) References Cited

U.S. PATENT DOCUMENTS

| | | | | |
|---|---|---|---|---|
| 2013/0319407 A1* | 12/2013 | Liu | ..................... | A61M 15/06 128/202.21 |
| 2014/0332019 A1* | 11/2014 | Liu | ..................... | A61M 15/06 131/329 |
| 2015/0136156 A1* | 5/2015 | Liu | ..................... | A24F 47/008 131/329 |

* cited by examiner

ATOMIZER AND ELECTRONIC CIGARETTE HAVING SAME

TECHNICAL FIELD

The present invention relates to electronic cigarettes, and particularly to an atomizer and an electronic cigarette using same.

BACKGROUND ART

In a typical electronic cigarette, the electronic cigarette includes a glass fiber core, and a heating wire wound around the glass fiber core. Two opposite ends of the glass fiber core extend into a liquid chamber to absorb tobacco liquid. Because a contact surface between the heating wire and glass fiber core is small, the glass fiber core may produce a scorched flavor due to the high temperature of some part of the glass fiber core after used for a long time.

What is needed, therefore, is an atomizer and an electronic cigarette using same, which can overcome the above shortcomings.

SUMMARY

An exemplary atomizer includes a shell, a liquid supply received in the shell, and an atomizing assembly. The liquid supply is configured for storing tobacco liquid, and the liquid supply has an open end. The atomizing assembly includes a liquid conducting element, a heating disk, and a liquid absorbing body. An end of the liquid conducting element is engaged in the open end. The heating disk is arranged at an opposite end of the liquid conducting element. The liquid absorbing body is sandwiched between the liquid conducting element and the heating disk. The liquid conducting element is configured for conveying the tobacco liquid from the liquid supply to the liquid absorbing body. The heating disk is configured for heating the tobacco liquid in the liquid absorbing body to vaporize.

BRIEF DESCRIPTION OF THE DRAWINGS

Many aspects of the present disclosure can be better understood with reference to the following drawings. The components in the drawings are not necessarily drawn to scale, the emphasis instead being placed upon clearly illustrating the principles of the present disclosure. Moreover, in the drawings, like reference numerals designate corresponding parts throughout the several views.

DETAILED DESCRIPTION

Figure 1:
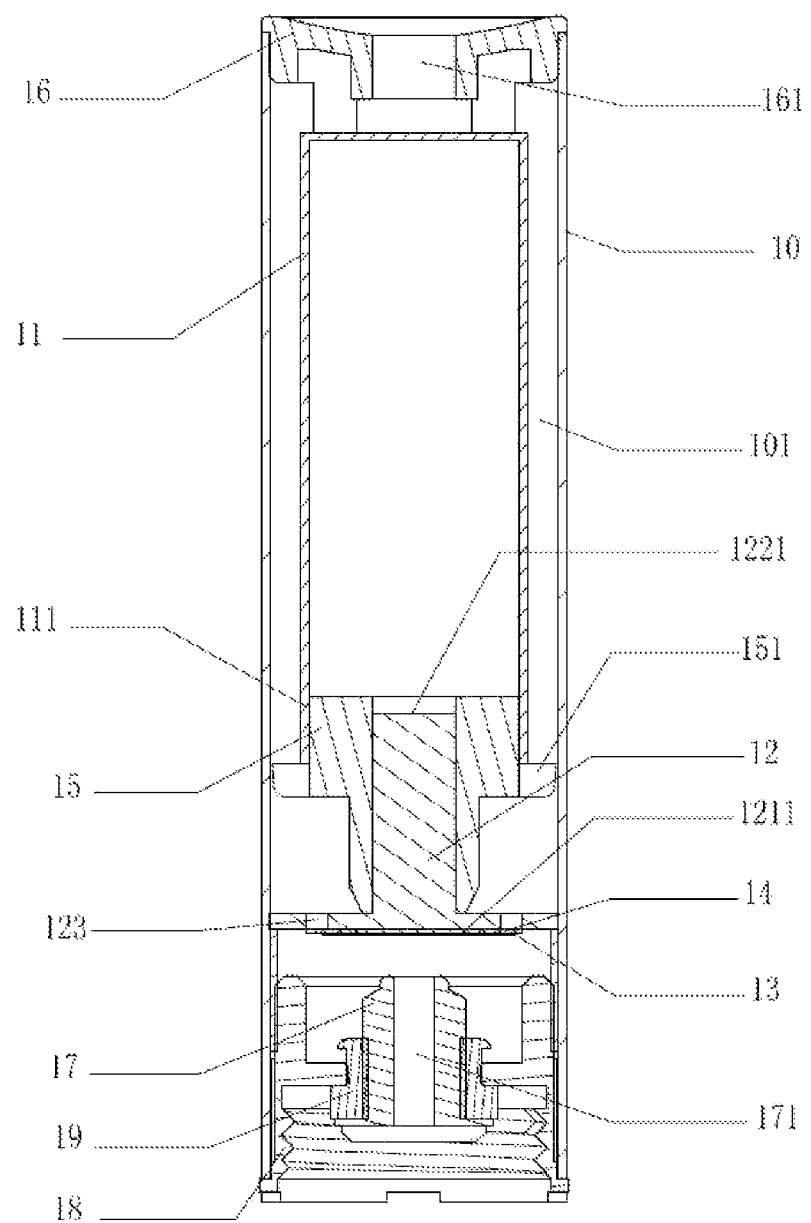
FIG. 1 is a cross-sectional view of an atomizer according to a first embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts have been exaggerated to better illustrate details and features of the present disclosure.

The disclosure is illustrated by way of example and not by way of limitation in the figures of the accompanying drawings in which like references indicate similar elements. It should be noted that references to "an" or "one" embodiment in this disclosure are not necessarily to the same embodiment, and such references mean at least one.

Several definitions that apply throughout this disclosure will now be presented.

The term "outside" refers to a region that is beyond the outermost confines of a physical object. The term "inside" indicates that at least a portion of a region is partially contained within a boundary formed by the object. The term "substantially" is defined to be essentially conforming to the particular dimension, shape or other word that substantially modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

Referring to FIG. 1, an atomizer includes a shell 10, a liquid supply 11 received in the shell 10, and an atomizing assembly. The liquid supply 11 is configured (i.e., structured and arranged) for storing tobacco liquid. The atomizing assembly includes a liquid conducting element 12, a heating disk 13, and a liquid absorbing body 14. The liquid supply 11 includes an open end 111. The liquid conducting element 12 inserts the open end 111. The liquid conducting element 12 is made of porous ceramic, porous metal, or porous fiber. The liquid conducting element 12 is adapted for absorbing and conveying the tobacco liquid. The liquid conducting element 12 includes a first end surface 1221 and a second end surface 1211. The first end surface 1221 is in contact with the tobacco liquid in the liquid supply 11. The heating disk 13 is arranged on the second end surface 1211, and is configured for heating the tobacco liquid in the liquid conducting element 12 to vaporize.

Figure 2:
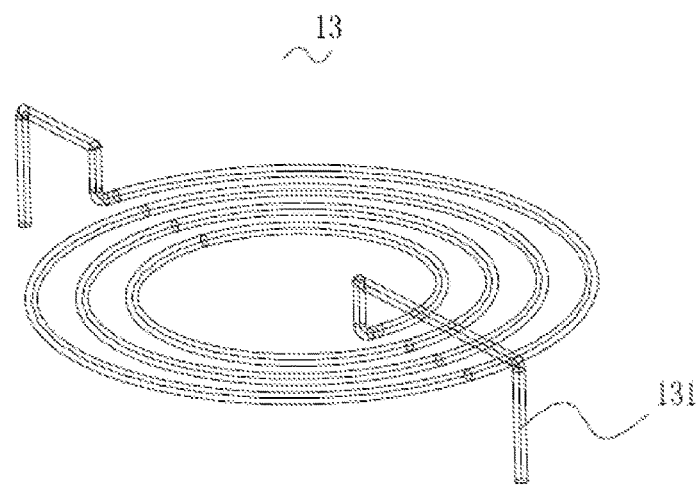
FIG. 2 is a perspective view of a heating disk of the atomizer of FIG. 1.

Referring to FIG. 2, the heating disk 13 is formed by winding a heating wire to form a disk shape. The liquid absorbing body 14 is sandwiched between the heating disk 13 and the second end surface 1211. In the present embodiment, the liquid absorbing body 14 is made of fiber cloth, e.g., glass fiber cloth, ceramic fiber cloth. The liquid absorbing body 14 is configured for absorbing tobacco liquid. The heating disk 13 is not in direct contact with the second end surface 1211. When the user of the atomizer activates the atomizer, the heating disk 13 heats the tobacco liquid in the liquid absorbing body 14 to form aerosol. When the atomizer stops working, the liquid absorbing body 14 prevents liquid leakage from the second end surface 1211 of the liquid conducting element 12.

Figure 3:
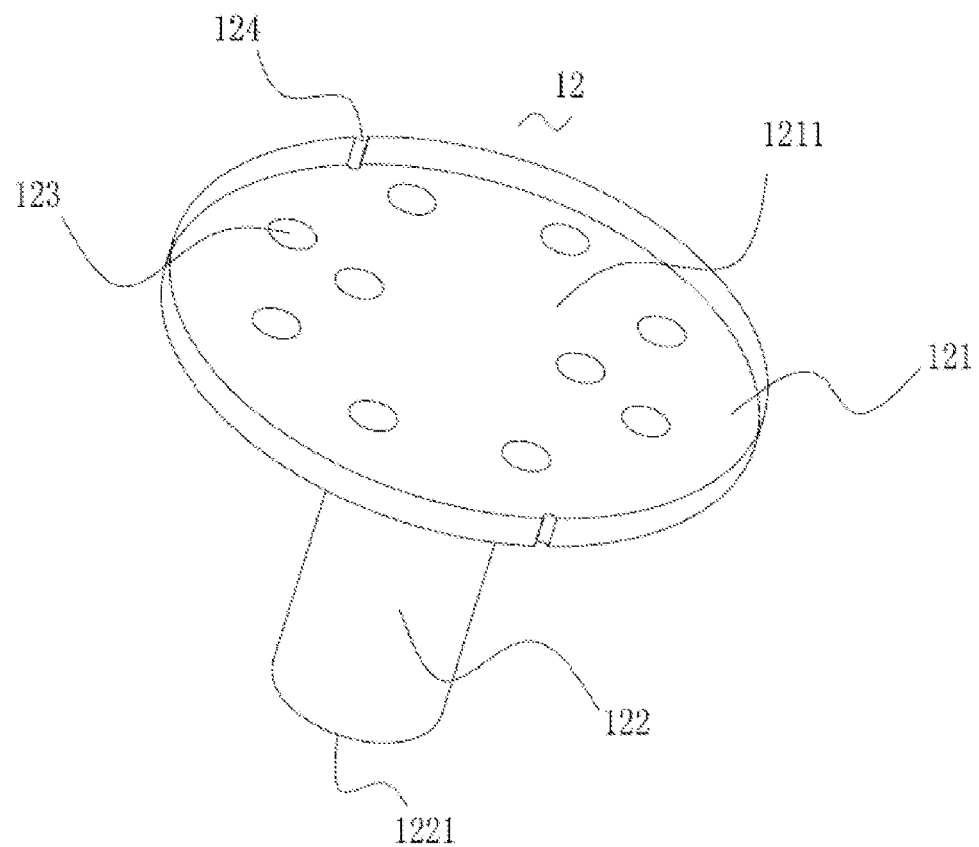
FIG. 3 is a perspective view of a liquid conducting element of the atomizer of FIG. 1.

Referring to FIG. 3, the liquid conducting element 12 is T-shaped. The liquid conducting element 12 includes a bottom plate 121, and a column-shaped part 122 extending from the bottom plate 121. The first end surface 1221 is an end surface of the column-shaped part 122. The column-shaped part 122 is engaged in the open end 111. The second end surface 1211 is a bottom surface of the bottom plate 121. The bottom plate 121 defines a plurality of air holes 123 in the second end surface 1211, and two grooves 124 in a sidewall thereof. Two wire ends of the heating disk 13 pass through two air holes 123, and are then received in the grooves 124. In this way, the heating disk 13 is fixed in the liquid conducting element 12, and the liquid absorbing body 14 is tightly sandwiched between the heating disk 13 and the second end surface 1211. The atomizer further includes a silica sleeve 15 engaged in the open end 111 of the liquid supply 11. The silica sleeve 15 and the column-shaped part 122 cooperatively seal tobacco liquid in the liquid supply 11. The silica sleeve 15 tightly nests the column-shaped part 122. The silica sleeve 15 includes a protruding stage 151 for positioning the liquid supply 11 when assembling the liquid supply 11.

Referring to FIG. 1 again, the atomizer further includes a mouthpiece 16. The mouthpiece 16 defines an air outlet 161, and is arranged at one end of the shell 10 adjacent to the liquid supply 11. The atomizer further includes an electrode assembly at an end of the shell 10 near the heating disk 13. The electrode assembly is configured for connecting with an external power supply. In the present embodiment, the electrode assembly includes at least two threaded electrodes 17, 18 and an electrical insulator 19 disposed between the electrodes 17, 18. The electrode assembly defines a through hole 171. The shell 10 and the liquid supply 11 cooperatively define an air passage 101. When the user smokes, air enters the air passage 101 via the through hole 171, and passes through the air hole 123. The aerosol formed by the heating disk 13 goes along the air passage 101, through the air outlet 161, and then reaches the mouth of the user.

Figure 4:
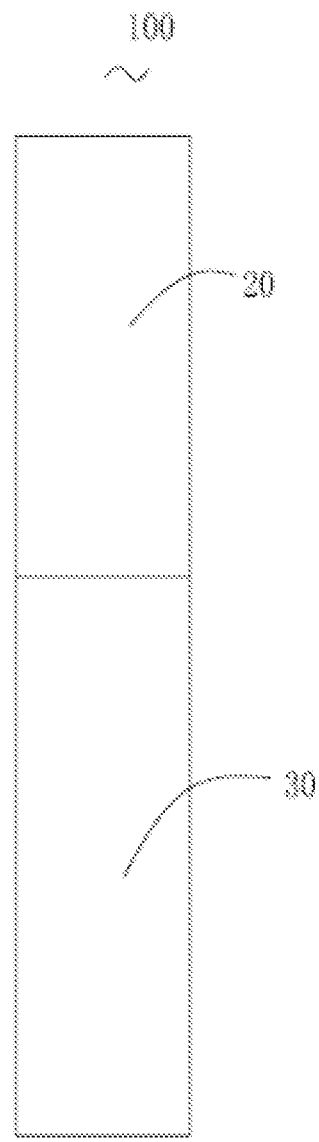
FIG. 4 is a side view of an electronic cigarette according to a second embodiment.

Referring to FIG. 4, an electronic cigarette 100 includes an atomizer 20 according to the first embodiment, and a power supply 30. The power supply 30 is configured for supplying the atomizer 20 power.

It is understood that the above-described embodiments are intended to illustrate rather than limit the disclosure. Variations may be made to the embodiments and methods without departing from the spirit of the disclosure. Accordingly, it is appropriate that the appended claims be construed broadly and in a manner consistent with the scope of the disclosure.

What is claimed is:

1. An atomizer, comprising:
a shell;
a liquid supply received in the shell, the liquid supply being configured for storing tobacco liquid, the liquid supply having an open end; and
an atomizing assembly, the atomizing assembly comprising:
a liquid conducting element, an end of the liquid conducting element being engaged in the open end;
a heating disk arranged at an opposite end of the liquid conducting element, two connective ends of the heating disk extending out from the heating disk; and
a liquid absorbing body sandwiched between the liquid conducting element and the heating disk, the liquid conducting element being configured for conveying the tobacco liquid from the liquid supply to the liquid absorbing body, the heating disk being configured for heating the tobacco liquid in the liquid absorbing body to vaporize, wherein the liquid conducting element comprises a plurality of air holes, each of the two connective ends of the heating disk to a power supply extends to pass the liquid absorbing body and pass through one of the plurality of air holes of the liquid conducting element, and extends toward a side edge of the liquid conducting element along a surface of the liquid conducting element facing away from the liquid absorbing body to subsequently pass by the liquid conducting element, and pass by the liquid absorbing body and the heating disk in order to fix the heating disk, the liquid absorbing body and the liquid conducting element together.

2. The atomizer according to claim 1, wherein the heating disk comprises a heating wire spirally wound to form a disk shape, the two connective ends are located and defined at two distal ends of the heating wire, respectively.

3. The atomizer according to claim 1, wherein the liquid conducting element is made of material selected from a group consisting of porous ceramic, porous metal, and porous fiber.

4. The atomizer according to claim 1, wherein the liquid absorbing body is made of fiber cloth.

5. The atomizer according to claim 1, wherein the liquid conducting element comprises a bottom plate and a column-shaped part extending from the bottom plate, the bottom plate is in contact with the liquid absorbing body, and the column-shaped part is engaged in the open end.

6. The atomizer according to claim 5, further comprising a silica sleeve, wherein the silica sleeve is engaged in the open end, and nests the column-shaped part of the liquid conducting element, the silica sleeve and the column-shaped part cooperatively seal the liquid supply.

7. The atomizer according to claim 6, wherein the silica sleeve comprises a protruding stage for positioning the liquid supply.

8. The atomizer according to claim 5, wherein the bottom plate defines the plurality of air holes for air to pass therethrough.

9. The atomizer according to claim 8, wherein the bottom plate further defines two grooves in a sidewall thereof, the two connective ends of the heating disk are received in the two grooves respectively when passing through the side edge of the liquid conducting element.

10. The atomizer according to claim 1, further comprising an electrode assembly arranged at one end of the shell, wherein the electrode assembly is adapted for connecting with an external power supply.

11. An electronic cigarette, comprising:
an atomizer according to claim 1;
a power supply configured for supplying power to the atomizer.

12. The electronic cigarette according to claim 11, wherein the heating disk comprises a heating wire spirally wound to form a disk shape.

13. The electronic cigarette according to claim 11, wherein the liquid conducting element is made of material selected from a group consisting of porous ceramic, porous metal, and porous fiber.

14. The electronic cigarette according to claim 11, wherein the liquid absorbing body is made of fiber cloth.

15. The electronic cigarette according to claim 11, further comprising a silica sleeve, wherein the silica sleeve is engaged in the open end, and nests the column-shaped part of the liquid conducting element, the silica sleeve and the column-shaped part cooperatively seal the liquid supply.

16. The electronic cigarette according to claim 15, wherein the silica sleeve comprises a protruding stage for positioning the liquid supply.

17. The electronic cigarette according to claim 11, wherein the bottom plate further defines two grooves in a sidewall thereof, two connective ends of the heating disk to the power supply are received in the two grooves respectively when passing through a side edge of the liquid conducting element.

* * * * *